US00PP28268P3

(12) United States Plant Patent
Sproul

(10) Patent No.: US PP28,268 P3
(45) Date of Patent: Aug. 15, 2017

(54) ***FLORIBUNDA* ROSE PLANT NAMED 'SPROSUL'**

(50) Latin Name: ***Rosa hybrida*/Floribunda Rose Plant**
Varietal Denomination: cv. Sprosul

(71) Applicant: CP DELAWARE, INC.

(72) Inventor: James A. Sproul, Bakersfield, CA (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 83 days.

(21) Appl. No.: 14/756,260

(22) Filed: Aug. 20, 2015

(65) Prior Publication Data

US 2017/0055403 P1 Feb. 23, 2017

(51) Int. Cl.
*A01H 5/02* (2006.01)

(52) U.S. Cl.
USPC ..... Plt./149

(58) Field of Classification Search
USPC ..... Plt./149–151, 141–142
See application file for complete search history.

*Primary Examiner* — Anne Grunberg
(74) *Attorney, Agent, or Firm* — Buchanan Ingersoll & Rooney PC

(57) ABSTRACT

A new and distinct variety of Floribunda rose plant is provided which forms in abundance on a substantially continuous basis attractive semi-double cup-shaped blossoms that are primarily deep magenta pink in coloration. The vegetation is vigorous and strong and the growth habit is bushy and upright. Attractive ornamental medium green foliage with a glossy aspect on the upper surface is formed. The plant is particularly well suited for growing in a Western landscape. Excellent resistance to rust and mildews has been displayed during observations to date. Distinctive ornamentation is provided.

1 Drawing Sheet

Botanical/commercial classification: *Rosa hybrida*/Floribunda Rose Plant.

Varietal denomination: cv. Sprosul.

SUMMARY OF THE INVENTION

The new variety of Floribunda rose plant of the present invention was created by artificial pollination that was carried out during the spring of 2009 at Bakersfield, Calif., U.S.A., wherein two parents were crossed which previously had been studied in the hope that they would contribute the desired characteristics. The female parent (i.e., seed parent) was the 'Wekfabpur' variety (U.S. Plant Pat. No. 16,623). The male parent (i.e., pollen parent) was an unnamed and unreleased seedling (non-patented in the United States).

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) abundantly and substantially continuously forms attractive cup-shaped semi-double blossoms that are primarily deep magenta pink coloration,
(b) exhibits a bushy and upright growth habit,
(c) forms vigorous vegetation,
(d) forms attractive ornamental medium green foliage with a glossy aspect on the upper surface,
(e) exhibits excellent resistance to rust and mildews, and
(f) is well suited for providing distinctive ornamentation.

A new rose variety is provided having distinctive deep magenta pink blossoms, combined with substantially continuous blooming. The plant was found to rebloom well and displays an attractive vigorous upright and bushy growth habit. The intensity of the blossom color may vary somewhat depending upon the growing conditions that are encountered.

The new variety well meets the needs of the horticultural industry particularly when grown in the Western landscape an can be grown to advantage as attractive ornamentation in parks, gardens, public areas, and residential landscapes. The deep magenta pink blossom coloration contrasts nicely with the medium green foliage.

The new variety can be readily distinguished from its parental varieties and previously known Floribunda varieties. More specifically, while the new variety forms blossoms that are mostly deep magenta pink in color, transitioning to yellow in color at the point of attachment, the 'Wekfabpur' female parent forms dissimilar purple-colored blossoms. Further, the male parent was an unnamed shrub rose that possessed yellow and orange striped blossoms, while the new variety is a floribunda rose with blossoms that are mostly deep magenta pink in color, transitioning to yellow in color at the point of attachment. Also, when compared to the 'Wekvossutono' variety (U.S. Plant Pat. No. 18,473), it is observed that the 'Wekvossutono' variety is very double and commonly displays blossoms having approximately 30 to 45 petals, while the new variety displays blossoms having approximately 12 petals on average.

The characteristics of the new variety have been found to be homogeneous and stable and are strictly transmissible by asexual propagation by the use of cuttings from one generation to another at Wasco, Calif., U.S.A. Accordingly, the new variety can be asexually reproduced in a true-to-type manner.

The new variety has been named 'Sprosul', and will be marketed under the SULTRY SANGRIA trademark.

BRIEF DESCRIPTION OF THE PHOTOGRAPH

The accompanying photograph shows, as nearly true as it is reasonably possible to make the same in a color illustration of this character, typical blossoms and foliage of the new variety. The illustrated plant was approximately two years of age and was growing outdoors during May 2014 on its own roots in a container at West Grove, Pa., U.S.A.

DETAILED BOTANICAL DESCRIPTION

The chart used in the identification of colors is that of The Royal Horticultural Society (R.H.S. Colour Chart—1995 Edition or equivalent). The description is based on the observation of two-year-old specimens of the new variety during June while growing outside in containers on their own roots at West Grove, Pa., U.S.A.

Class: Floribunda.

Plant:

*Height*.—Approximately 1.7 m when mature.

*Width*.—Approximately 1 m when mature.

*Habit*.—Bushy and upright.

Branches:

*Color*.—Young stems: near Green Group 137C. Adult wood: near Brown Group 200D.

*Size*.—Main stems commonly are approximately 7.5 cm in length on average, and secondary stems commonly are approximately 22.5 cm in length on average.

*Thorns*.—Size: young thorns: commonly approximately 1 cm in length on average, and approximately 6 mm in width on average. Size: mature thorns: commonly approximately 9 mm in length on average, and approximately 5 mm in width on average. Color on young stems: near Yellow-Green Group 144B. Color on mature wood: near Yellow-Green Group 144B.

Leaves:

*Size*.—A five-leaflet leaf commonly is approximately 10 cm in length on average, and approximately 7.5 cm in width on average. General appearance: dark green.

*Leaflets*.—Number: 3, 5, and 7. Shape: ovate with a serrate margin. Texture (upper surface): glabrous and glossy. Texture (under surface): smooth with a glossy upper surface. Size: terminal leaflets commonly are approximately 5.5 cm in length on average and approximately 3 cm in width on average, and lower leaflets commonly are approximately 3 cm in length on average and approximately 1.5 cm in width on average. Color (young foliage): Yellow-Green Group 144A on the upper surface, and Green Group143C on the under surface. Color (fully mature foliage): commonly near Green Group 137A on the upper surface, and Green Group 137C on the under surface.

Inflorescence:

*Number of flowers*.—Commonly in clusters of up to approximately 3 to 7 blossoms per stem on average, and commonly approximately 65 flowers on a plant at a given time.

*Peduncle*.—Smooth with short pubescence in texture, near Green Group 143C in coloration, approximately 4 cm in length on average, and approximately 2 mm in diameter on average.

*Sepals*.—Number: Five. Length: commonly approximately 1.8 cm on average. Width: commonly approximately 7 mm on average. Margin: entire, and commonly two or three sepals bear extensions of approximately 5 mm in length and approximately 1 mm in width. Upper surface: near Yellow-Green Group 147C, smooth, and covered with short hairs. Under surface: smooth, and near Green Group 143B in coloration.

*Buds*.—Shape: ovoid. Length: approximately 2 cm on average. Diameter: commonly approximately 1 cm on average. Color: near Red-Purple Group 59A blending to near Yellow Group 4A at the base.

*Flower*.—Form: Semi-double. Diameter: approximately 2.5 cm on average. Shape: cup-like. Color (when opening begins): Upper surface: near Red-Purple Group 60B transitioning to near Yellow Group 4D at the point of attachment. Under surface: near Red Group 63A transitioning to near Yellow Group 4D at the base. Color (at end of blooming): Upper surface: near Red-Purple Group 72A transitioning to near Yellow Group 4D at the point of attachment. Under surface: near Red-Purple Group 72B transitioning to near Yellow Group 4D at the point of attachment. Fragrance: light. Petal shape: obcordate. Petal length: commonly approximately 2 cm on average. Petal width: commonly approximately 2 cm on average. Petal margin: entire and wavy. Petal apex: obcordate. Petal base: rounded. Petal number: approximately 12 on average. Petal drop: good, with the petals commonly dropping cleanly and freely. Stamen number: approximately 75 on average. Anthers: near Greyed-Orange Group 163A in coloration. Filaments: near Yellow Group 11A in coloration, and approximately 8 mm in length. Pollen: commonly present in a moderate quantity, and near Greyed-Orange Group 163A in coloration. Pistils: separate and free, and commonly approximately 18 in number on average. Stigmas: near Yellow Group 2B in coloration, and approximately 1 mm in size. Styles: commonly near Yellow Group 2B on the approximately bottom half and near Red-Purple Group 60A on the approximately top half, and approximately 1 cm in length. Receptacle: substantially round in shape, smooth with short pubescence, achenes stand on the bottom and wall, approximately 5 mm in diameter, and near Yellow-Green Group 144A in coloration.

Development:

*Vegetation*.—Dark green, vigorous and strong.

*Blossoming*.—Abundant and substantially continuous from spring to frost.

*Resistance to diseases*.—Excellent with respect to rust and mildews.

*Propensity to form hips/seeds*.—None observed at this time.

*Hardiness*.—U.S.D.A. Hardiness Zone Nos. 6 to 9.

Plants of the new 'Sprosul' variety have not been observed under all possible environmental conditions to date. Accordingly, it is possible that the phenotypic expression may vary somewhat with changes in light intensity and duration, cultural practices, and other environmental conditions.

I claim:

1. A new and distinct variety of Floribunda rose plant characterized by the following combination of characteristics:

(a) abundantly and substantially continuously forms attractive cup-shaped semi-double blossoms that are primarily deep magenta pink in coloration, (b) exhibits a bushy and upright grown habit, (c) forms vigorous vegetation.

(d) forms attractive ornamental medium green foliage with a glossy aspect on the upper surface, (e) exhibits excellent resistance to rust and mildews, and (f) is well suited for providing distinctive ornamentation;

substantially as herein shown and described.

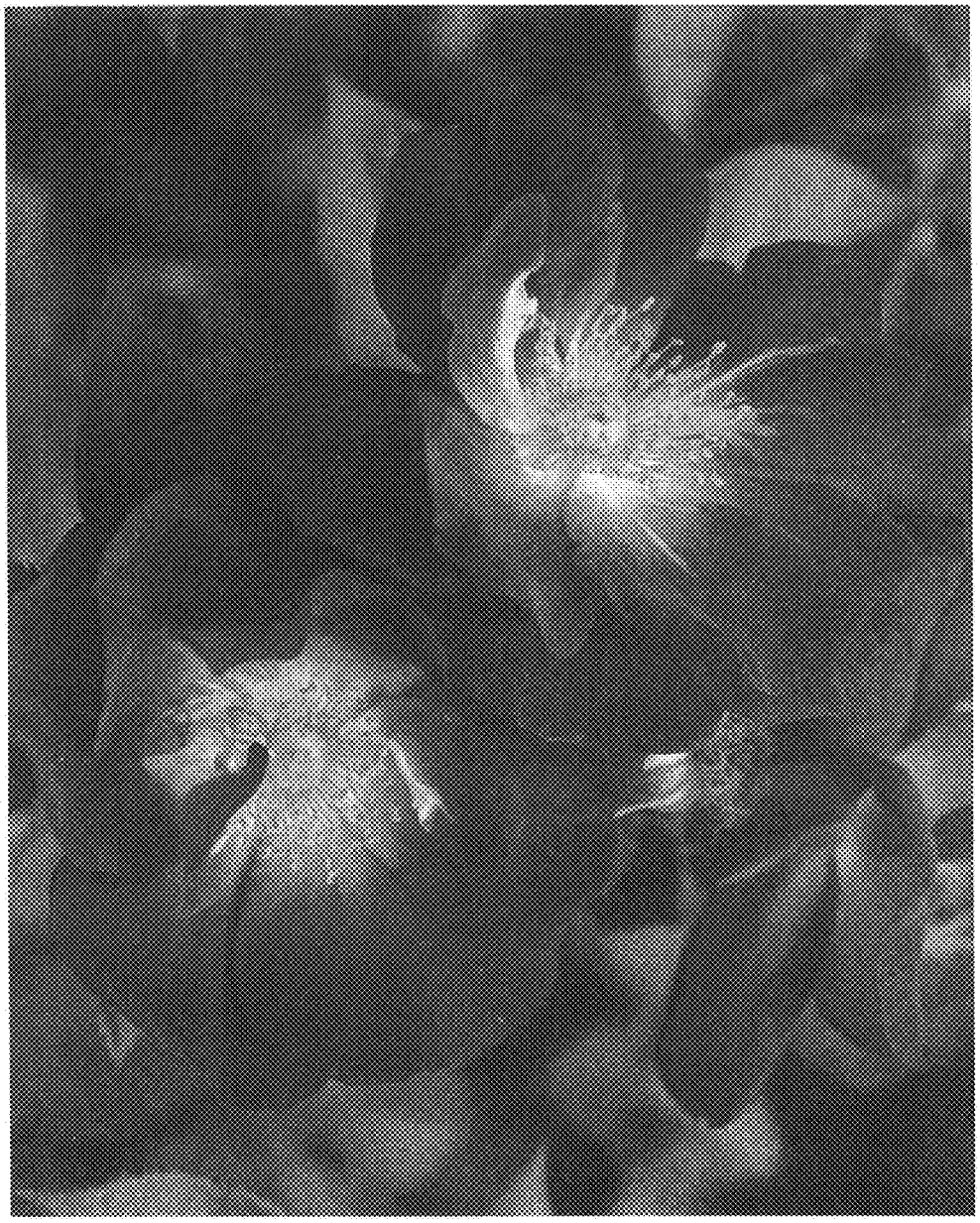

* * * * *